United States Patent
Kratzer et al.

(10) Patent No.: US 7,771,052 B2
(45) Date of Patent: Aug. 10, 2010

(54) METHOD FOR PERFORMING A CONTRAST VISION TEST

(75) Inventors: Timo Kratzer, Aalen (DE); Erich Hofmann, Aalen (DE); Lars Mendel, Aalen (DE)

(73) Assignee: Carl Zeiss Vision GmbH (DE)

( * ) Notice: Subject to any disclaimer, the term of this patent is extended or adjusted under 35 U.S.C. 154(b) by 340 days.

(21) Appl. No.: 11/719,421

(22) PCT Filed: Sep. 10, 2005

(86) PCT No.: PCT/EP2005/009735

§ 371 (c)(1),
(2), (4) Date: May 16, 2007

(87) PCT Pub. No.: WO2006/056252

PCT Pub. Date: Jun. 1, 2006

(65) Prior Publication Data

US 2008/0137037 A1 Jun. 12, 2008

(30) Foreign Application Priority Data

Nov. 19, 2004 (DE) ................. 10 2004 055 754

(51) Int. Cl.
*A61B 3/02* (2006.01)
*A61B 3/10* (2006.01)
(52) U.S. Cl. .............. 351/239; 351/205; 351/221
(58) Field of Classification Search ................ 351/239, 351/200, 205, 246, 221–222
See application file for complete search history.

(56) References Cited

U.S. PATENT DOCUMENTS

| 4,293,200 A | 10/1981 | Dobson et al. |
| 4,511,228 A * | 4/1985 | von Gierke et al. ......... 351/243 |
| 5,500,699 A | 3/1996 | Ginsburg |
| 5,589,897 A | 12/1996 | Sinclair et al. |
| 2003/0174284 A1 | 9/2003 | Stewart |
| 2007/0076168 A1* | 4/2007 | Ellenbogen ................. 351/200 |

FOREIGN PATENT DOCUMENTS

DE 3009049 A1 9/1980

OTHER PUBLICATIONS

Article published at: http://www.psych.ndsu.nodak.edu/mccourt/Psy460/Spatial%20frequency%20analysis/Spatial%20frequency%20analysis.html Spatial Frequency Analysis, Beyond Acuity: The Contrast Sensitive Function. Copyright 1997 [Mark E. McCourt]. Revised Jan. 4, 2001.

* cited by examiner

*Primary Examiner*—Scott J Sugarman
*Assistant Examiner*—Dawayne A Pinkney
(74) *Attorney, Agent, or Firm*—GrayRobinson, P.A.

(57) ABSTRACT

The invention relates to a method for performing a contrast vision test on a subject in order to determine a contrast sensitivity function. According to said method, an image of a continuous sinusoidal grid is presented to the subject for viewing, the spatial frequency continuously changes in the direction of a first axis, and the contrast continuously changes in the direction of a second axis that extends perpendicular to the first axis. The subject's contrast sensitivity function is defined by means of a curve that encloses an area of the sinusoidal grid in which the subject perceives the sinusoidal grid pattern during viewing.

20 Claims, 2 Drawing Sheets

METHOD FOR PERFORMING A CONTRAST VISION TEST

CROSS-REFERENCE TO RELATED APPLICATION

This application is a U.S. National Phase Entry Under 35 U.S.C. §371 of, and claims priority under 35 U.S.C. §§119 and 363 to copending PCT/EP2005/009735, filed Sep. 10, 2005 which designated the U.S. and which claims priority to German Patent Application No. 10 2004 055 754.3, filed Nov. 19, 2004.

BACKGROUND OF THE INVENTION

1. Field of the Invention

The invention relates to a method for performing a contrast vision test in a subject in order to determine a contrast sensitivity function. The invention likewise relates to a computer program for performing the method, and also to a computer program product and a computer for executing the computer program.

2. Description of the Related Art

In contrast vision tests, a subject's ability to see contrasts is determined with the aid of a contrast sensitivity function. This is done in the case of previous appliances and measurement methods by measuring discrete visual acuity and contrast values. Suitable measurement objects used here are, as known for example from U.S. Pat. No. 5,500,699, Landolt rings and also letters of different sizes with specific discrete contrast values. In addition, sinusoidal gratings having a specific fixed frequency, i.e. spatial frequency, and a specific contrast value are sometimes used.

Tests of this kind have been used hitherto only for partially sighted persons or to diagnose pathological changes in the visual apparatus. The evaluation is usually carried out by registering the discrete points in a visual acuity/contrast scheme and visually comparing various registered data items.

The individual contrast sensitivity function can provide information on the eyesight or on eyesight problems even in normally ametropic persons. The discrete gradations of the known contrast vision tests are, however, too crude for this group of persons. Previous tests furthermore do not cover the entire contrast and visual acuity range applicable to normally ametropic persons. The previous evaluation methods also involve the problem that no continuous data which would enable automatic further processing is digitally registered.

Furthermore, no meaningful metric which can be used to describe the contrast sensitivity function exists as yet.

The present invention is therefore based on the object of providing a method of the kind mentioned in the introduction, which avoids the disadvantages of the prior art and in particular makes available a meaningful contrast vision test for determining a contrast sensitivity function even in normally ametropic subjects.

SUMMARY OF THE INVENTION

This object is achieved according to the invention by a method for performing a contrast vision test in a subject in order to determine a contrast sensitivity function, wherein an image of a continuous sinusoidal grating is displayed for the subject to view, in which grating the spatial frequency continuously changes in the direction of a first axis and in which the contrast continuously changes in the direction of a second axis which is perpendicular to the first axis, with the contrast sensitivity function of the subject being defined by a curve which encloses an area of the sinusoidal grating, in which the subject perceives the sinusoidal grating pattern during viewing.

The method proposed for performing a contrast vision test in a subject in order to determine a contrast sensitivity function is based on a continuous sinusoidal grating, in which the frequency of the sinusoidal grating continuously changes on one axis, i.e. the visual acuity or the angle of view which is discernable to the subject changes, while the contrast of the sinusoidal grating on the axis which is perpendicular to it varies continuously. The contrast vision test according to the invention permits the determination of the individual contrast sensitivity function for every subject. This function is that enveloping curve below which the subject can still discern a grating pattern. The individual contrast sensitivity function can advantageously also be determined in normally ametropic subjects because the fine continuous resolution of the sinusoidal grating is ideal for this group of persons. The contrast vision test proposed can cover the entire contrast and visual acuity range applicable to normally ametropic persons.

Also proposed for performing the method according to the invention are a computer program, a computer program product and a computer for executing the computer program.

Further advantageous embodiments and developments of the invention follow from the remaining subclaims. An exemplary embodiment of the invention is illustrated in principle below with reference to the drawings.

DETAILED DESCRIPTION

Figure 1:
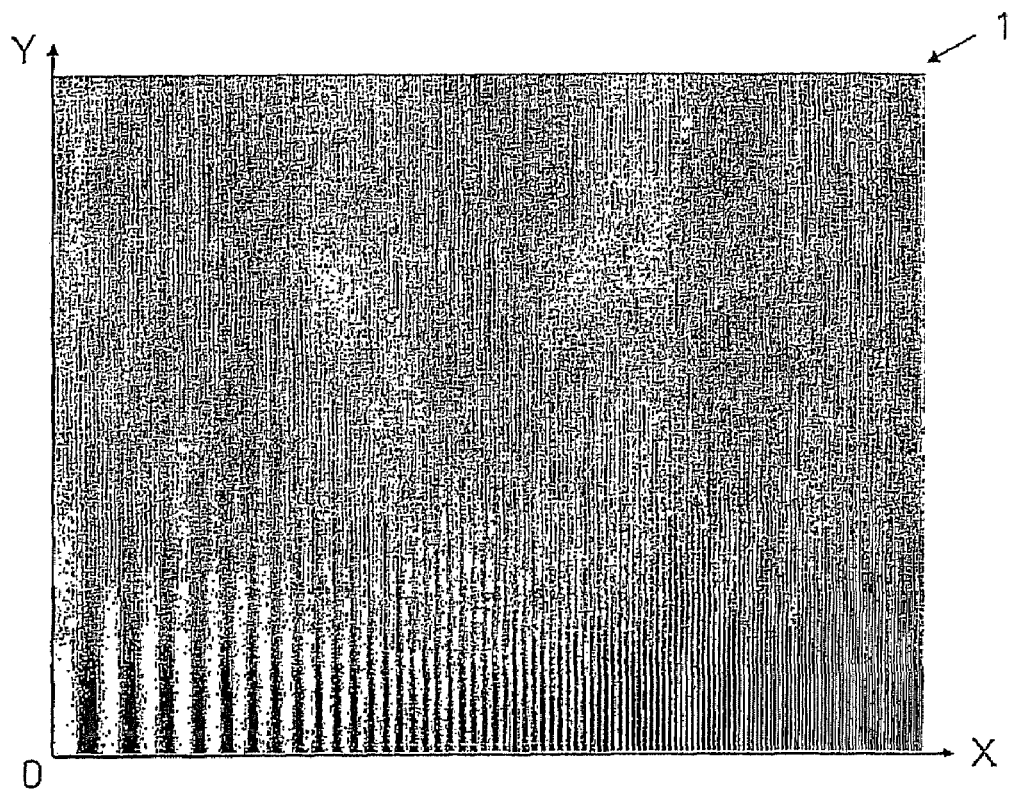
FIG. 1 shows an illustration of a continuous sinusoidal grating for use in a method according to the invention.
Figure 2:
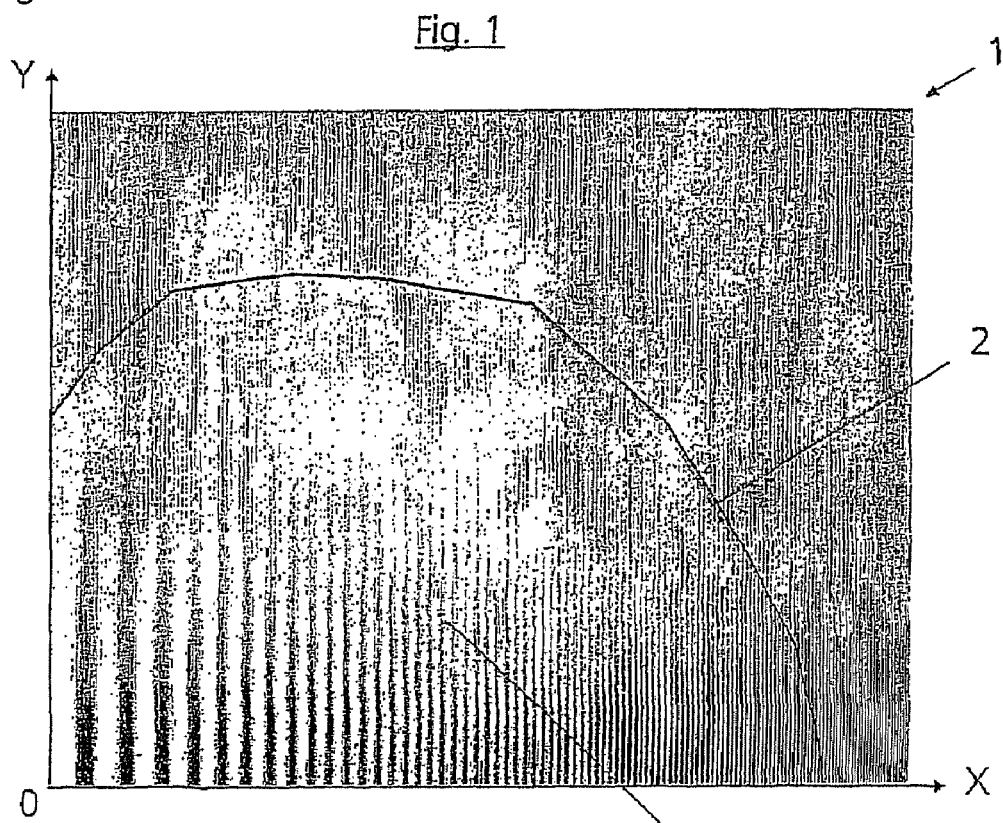
FIG. 2 shows an illustration of the continuous sinusoidal grating according to FIG. 1 with a marked contrast sensitivity curve.

In a method for performing a contrast vision test in a subject in order to determine a contrast sensitivity function, an image of a continuous sinusoidal grating 1 illustrated in FIG. 1 is displayed for the subject to view, in which grating the spatial frequency continuously changes in the direction of an X axis, i.e. in the present case increases starting from a Y axis, and in which the contrast continuously changes on the Y axis which is perpendicular to the X axis, i.e. in the present case decreases starting from the X axis. The contrast sensitivity function of the subject is, as can be seen in FIG. 2, defined by a curve 2 enclosing an area 3 of the sinusoidal grating 1, in which the subject can still perceive or discern the sinusoidal grating pattern during viewing.

The spatial frequency and/or contrast ranges of the continuous sinusoidal grating 1 can be matched, i.e. the ranges which can be covered by the contrast vision test—both in the visual acuity direction (X) and also in the contrast direction (Y)—are matched to the desired requirements or to the subjects.

The method for performing a contrast vision test in a subject in order to determine a contrast sensitivity function is advantageously realized as a computer program on a computer. In further exemplary embodiments, the method according to the invention can of course also be performed using other auxiliary means. The computer program is executed by means of processing on a microprocessor of the computer. The computer program can be stored on a computer-readable data carrier (disk, CD, DVD, hard disk drive, USP memory stick or the like) or on an Internet server as computer program product, from where it can be transferred into a memory of the computer. The continuous sinusoidal grating 1 is imaged on a display device of the computer (not illustrated). For this, the computer, or the display device, must meet certain conditions. The resolution of the display device must be such that it permits error-free reproduction of the maximum frequency of the sinusoidal grating 1. In order to unambiguously obtain light and dark stripes, each light and dark stripe must be followed by a gray stripe. In order to achieve this it is necessary for the resolution of the display device or the reproduction appliance to be at least twice as high as is required for the display of the maximum visual acuity. The contrast ratio of the display device must be at least large enough for the desired number of different contrast stages to be displayed with adequate accuracy.

The subject now independently marks the curve or the contrast sensitivity function 2 in the sinusoidal grating 1 using an input appliance, in particular using a pointer appliance, preferably a mouse of the computer, with the marked curve being stored in the computer. This means that the subject can directly input his individual contrast sensitivity function using the mouse or another suitable input appliance (see FIG. 2).

If the display device of the computer or the image of the continuous sinusoidal grating 1 on the display device can be pivoted or rotated by 90 degrees with respect to the main viewing direction of the subject, it is also possible to register both the horizontal contrast sensitivity function and the vertical contrast sensitivity function of the subject.

It is also possible in particular to use the computer to adapt the minimum, the maximum and the average brightness of the sinusoidal grating 1 depending on the requirements. The primary color can furthermore be matched to the respective prerequisites. In the present case, the sinusoidal grating is in the form of a grayscale grating 1. Sinusoidal gratings with various hues of red, blue or green and also other color variants are also conceivable by way of example.

It is thus possible for a contrast vision test to be performed for all use and ambient conditions (ambient brightness, background brightness of the contrast vision test, glare, various visual aids or the like). Based on repeated performance of the contrast vision test at specified ambient conditions and continuous recording of data, it is possible to determine the individual contrast sensitivity function of the subject using statistical methods. The contrast vision test can also be performed under glare conditions by mounting a suitable illumination means near or in the region of the display device.

Various metrics can then be applied to the contrast sensitivity function in order to assess the curve or to compare different curves. Familiar metrics are, for example, the maximum visual acuity, the minimum contrast or the area under the contrast sensitivity curve 2.

Figure 3:
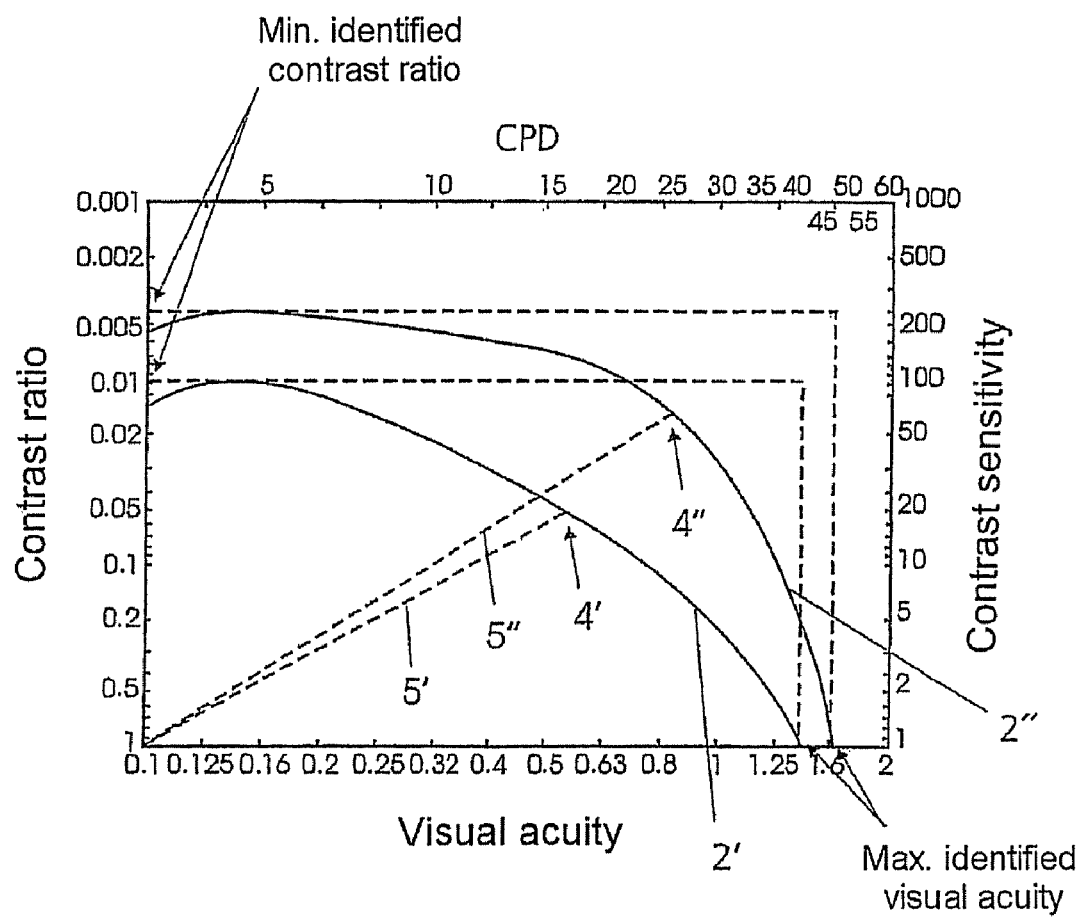
FIG. 3 shows a diagram of a metric for the assessment of two contrast sensitivity curves.

The metric used in FIG. 3 is a so-called Contrast Acuity Product (CAP). In this case, two contrast sensitivity functions 2', 2" are illustrated in a comparative manner. The diagram shows, in a logarithmic fashion, contrast ratio (left, vertical scale), visual acuity (bottom, horizontal scale), contrast sensitivity (right, vertical scale) and CPD, Cycles per Degree (top, horizontal scale). The calculation of the CAP includes multiplicatively the maximum identified visual acuity, the minimum identified contrast ratio and a shape or a bend of the contrast sensitivity curves 2', 2". The shape or the bending of the curves 2', 2" is defined by the points of intersection 4', 4" of the respective contrast sensitivity curves 2', 2" with the diagonal 5', 5" which is described by the rectangle with the corner points of maximum identified visual acuity, minimum visual acuity (here: 0.1), minimum discerned contrast, maximum contrast (here: 1.0).

The CAP is thus the product of the values of maximum discerned visual acuity of a contrast sensitivity curve 2', 2", minimum discerned contrast of a contrast sensitivity curve 2', 2" and the length of the straight line 5', 5" from the bottom left corner of the area shown to the abovedescribed point of intersection 4', 4" of a contrast sensitivity curve 2', 2".

What is claimed is:

1. A contrast vision test method for determining a contrast sensitivity function of a subject, said method comprising the steps of:
   (a) displaying visually to the subject, under a specified ambient viewing condition, a sinusoidal grating pattern, said grating pattern having a first axis, a second axis, a spatial frequency and a contrast, said spatial frequency changing continuously along said first axis, said contrast changing continuously along said second axis, said second axis being perpendicular to said first axis;
   (b) determining, based on a response of the subject to viewing said grating pattern under said ambient viewing condition of step (a), a visual contrast sensitivity curve of the subject which defines the ability of the subject to visually discern said grating pattern under said ambient viewing condition of step (a);
   (c) repeating steps (a) and (b) at least once with each respective repetition being carried out under a different respective said ambient viewing condition to determine at least one respective additional visual contrast sensitivity curve of the subject, each respective said additional visual contrast sensitivity curve defining the ability of the subject to visually discern said grating pattern under a respective one of said different ambient viewing conditions, and
   (d) statistically determining a contrast sensitivity function of the subject based on said visual contrast sensitivity curve and said at least one additional visual contrast sensitivity curve.

2. The method as claimed in claim 1, wherein said spatial frequency of said grating continuously increases in a direction of said first axis starting from said second axis and said contrast of said grating continuously decreases in a direction of said second axis starting from said first axis.

3. The method as claimed in claim 1, wherein said spatial frequency of said grating has a spatial frequency range which can be adapted.

4. The method as claimed in claim 1, wherein the contrast vision test is performed using a computer and said grating is displayed, as an image on a display device of said computer.

5. The method as claimed in claim 4, further comprising the steps of: (i) marking said curve on said display device, said marking step being carried out by the subject using an input appliance, and, (ii) storing said curve in said computer.

6. The method as claimed in claim 5, wherein said image of said grating on said computer display device can be pivoted by ninety degrees with respect to a viewing direction of the subject.

7. The method as claimed in claim 1, wherein said ambient viewing condition comprises a glare condition.

8. A computer program with program code means for carrying out all the steps of claim 1, if the program is executed on a computer.

9. A computer-readable data carrier having stored thereon computer program code which is executable a computer to cause said computer to carry out all of the steps of claim 1.

10. A contrast vision test apparatus, comprising: a computer with a display device and an input appliance, said computer being programmed to carry out all of the steps of claim 1 such that said grating is visually displayed on said display device and said response of the subject to viewing said grating is provided as an input to said computer provided using said input appliance.

11. The apparatus as claimed in claim 10, wherein said grating can be pivoted by ninety degrees with respect to a viewing direction of the subject.

12. The apparatus as claimed in 11, further comprising an illumination apparatus arranged in the region of said display device such that said ambient viewing condition comprises a glare condition.

13. The method as claimed in claim 1, wherein said contrast of said grating has a contrast range which can be adapted.

14. A method for performing a contrast vision test on a subject in order to determine a contrast sensitivity function, said method comprising the steps of:
   (a) displaying visually to the subject a sinusoidal grating pattern, said grating pattern having a first axis, a second axis, a spatial frequency and a contrast, said spatial frequency changing continuously along said first axis, said contrast changing continuously along said second axis, said second axis being perpendicular to said first axis;
   (b) determining a visual contrast sensitivity curve of the subject based on a response of the subject to viewing said grating pattern;
   (c) assessing said curve based on a metric, said metric being a metric calculable using a calculation which includes multiplicatively: (i) a maximum identified visual acuity of said curve on said first axis, (ii) a minimum identified contrast ratio of said curve on said second axis and (iii) a distance between a first point and a second point, said first point corresponding to a maximum contrast ratio and a minimum visual acuity, said second point corresponding to a point of intersection of said curve with a straight line extending between said first point and a corner point, said corner point corresponding to said minimum identified contrast ratio and said maximum identified visual acuity.

15. A computer program with program code means for carrying out all the steps of claim 14, if the program is executed on a computer.

16. A computer-readable data carrier having stored computer program code which is executable a computer to cause said computer to carry out all of the steps of claim 14.

17. A contrast vision test apparatus, comprising: a computer having a display device and an input appliance, said computer being programmed to execute all of the steps of claim 14 such that said sinusoidal grating is visually displayed on said display device and said response of the subject to viewing said grating is provided to said computer by way of said input appliance.

18. The apparatus as claimed in claim 17, wherein said grating displayed on said display device can be pivoted by ninety degrees with respect to a viewing direction of the subject.

19. The apparatus as claimed in 18, further comprising an illumination apparatus mounted for illuminating said display device such that said viewing condition comprises a glare condition.

20. The method as claimed in claim 17, wherein said contrast of said grating has a contrast range which can be adapted.

\* \* \* \* \*

UNITED STATES PATENT AND TRADEMARK OFFICE
CERTIFICATE OF CORRECTION

PATENT NO. : 7,771,052 B2  Page 1 of 1
APPLICATION NO. : 11/719421
DATED : August 10, 2010
INVENTOR(S) : Timo Kratzer et al.

It is certified that error appears in the above-identified patent and that said Letters Patent is hereby corrected as shown below:

Column 5, line 11 Claim 12
   delete "in 11," and insert --in claim 11,--

Column 6, line 27 Claim 17
   delete "in 18," and insert --in claim 18,--

Signed and Sealed this
Nineteenth Day of April, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,771,052 B2 | Page 1 of 1 |
| APPLICATION NO. | : 11/719421 | |
| DATED | : August 10, 2010 | |
| INVENTOR(S) | : Kratzer et al. | |

It is certified that error appears in the above-identified patent and that said Letters Patent is hereby corrected as shown below:

In the claims

Column 5, line 11, claim 12
    delete "in 11" and insert --in claim 11--

Column 6, line 27, claim 19
    delete "in 18," and insert --in claim 18,--

Signed and Sealed this
Nineteenth Day of January, 2016

Michelle K. Lee
*Director of the United States Patent and Trademark Office*